(12) United States Patent
Chenal et al.

(10) Patent No.: US 6,447,454 B1
(45) Date of Patent: Sep. 10, 2002

(54) ACQUISITION, ANALYSIS AND DISPLAY OF ULTRASONIC DIAGNOSTIC CARDIAC IMAGES

(75) Inventors: Cedric Chenal, Kirkland, WA (US); Pascal Roncalez, Bellevue, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/732,559

(22) Filed: Dec. 7, 2000

(51) Int. Cl.$^7$ ................................................ A61B 8/00
(52) U.S. Cl. ...................................................... 600/449
(58) Field of Search ................................ 600/443, 447, 600/467, 437, 444, 455, 466

(56) References Cited

U.S. PATENT DOCUMENTS

| | | | |
|---|---|---|---|
| 5,195,521 A | | 3/1993 | Melton, Jr. et al. |
| 5,360,006 A | * | 11/1994 | Geiset et al. ............... 600/467 |
| 5,450,850 A | | 9/1995 | Iinuma |
| 5,458,126 A | | 10/1995 | Cline et al. |
| 5,533,510 A | | 7/1996 | Koch, III et al. |
| 5,601,084 A | * | 2/1997 | Sheehan et al. ............ 600/443 |
| 5,785,654 A | | 7/1998 | Iinuma et al. |
| 5,797,396 A | | 8/1998 | Geiser et al. |
| 6,106,465 A | * | 8/2000 | Napolitano et al. ......... 600/443 |
| 6,106,466 A | | 8/2000 | Sheehan et al. |
| 6,217,520 B1 | * | 4/2001 | He et al. .................... 600/467 |

OTHER PUBLICATIONS

Giachetti, "On–line Analysis of Echocardiographic Image Sequence," Medical Image Analysis, Oxforc University Press, vol. 2, No. 3, 1998, p. 271.

Geiser, et al., "Autonomous Epicardial and Endocardial Boundary Detection in Echocardiographic Short–Axis Images," Journal of the American Society of Echocardiography, vol. 11, No. 4, 1998, pp. 338–348.

Bosch et al., "Overview of Automated Quantitation Techniques in 2D Echocardiography," What's New in Cardiobascular Imaging, Kluwer Academic Publishers, The Netherlands, 1998, pp. 370–371.

Nishiura et al., "Development of the Automated Contour Tracking (ACT) Method," Medical Review No. 68, Kansai Research Laboratories, Toshiba Corporation, Kobe, Japan, pp. 26–30.

Schiller et al., "Recommendations for Quantitation of the Left Ventricle by Two–Dimensional Echocardiography," Journal of the American Society of Enchocardiography, vol. 2, No. 5, Sep.–Oct. 1989, pp. 358–367.

Wilson et al., "Automated Analysis of Echocardiographic Apical 4–Chamber Images," Proceedings of SPIE Conference, Aug. 2000, whole document.

* cited by examiner

*Primary Examiner*—Francis J. Jaworski
*Assistant Examiner*—Maulin Patel
(74) *Attorney, Agent, or Firm*—W. Brinton Yorks, Jr.

(57) ABSTRACT

The end diastole and end systole images from an acquired cardiac loop are shown side by side on an image display for automatic border tracing. The border tracings can be used to calculate ejection fraction in real time. The cardiac loops may be first acquired then processed for automatic border definition, or the acquired images can be processed in real time to indicate their suitability for automatic border detection as they are acquired.

31 Claims, 13 Drawing Sheets

FIG. 4
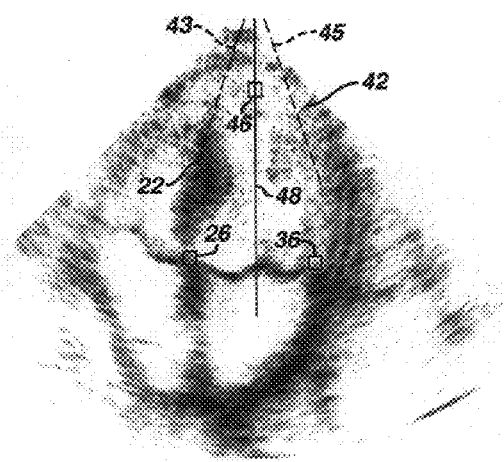
FIG. 5a
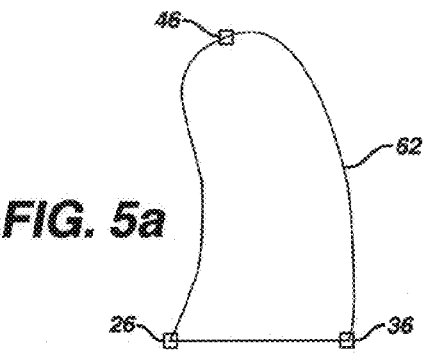
FIG. 5b  FIG. 5c
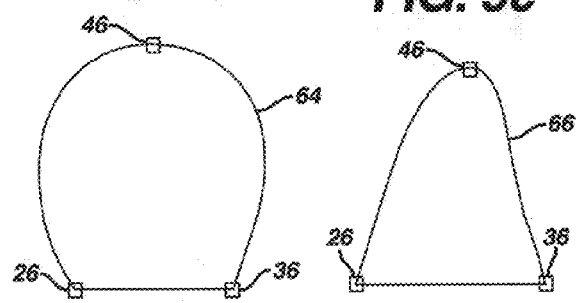

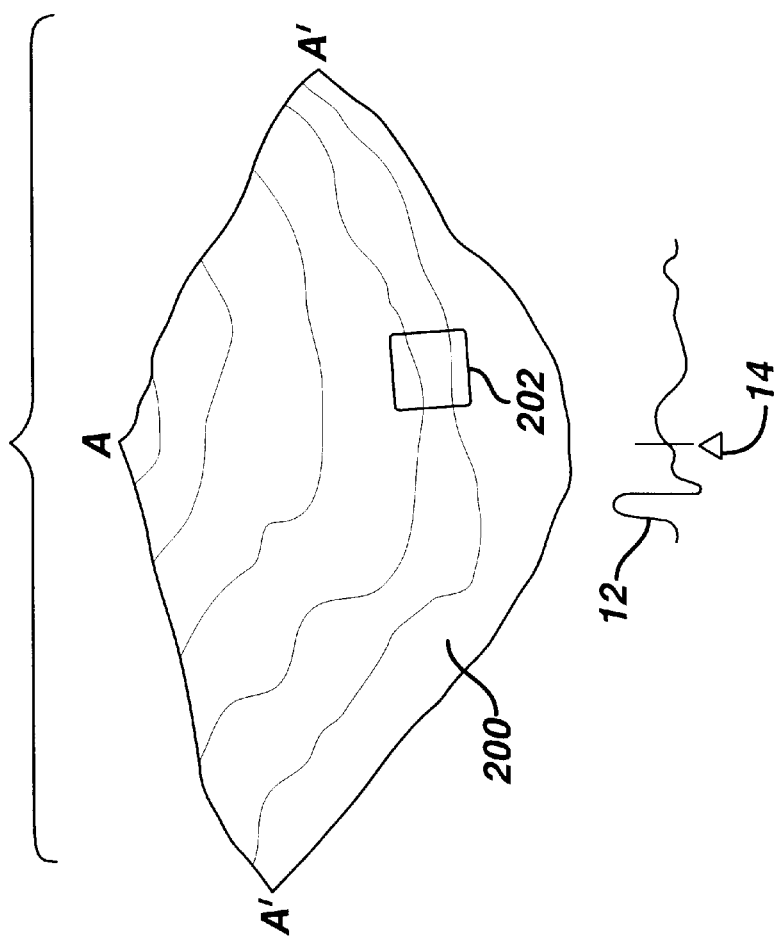
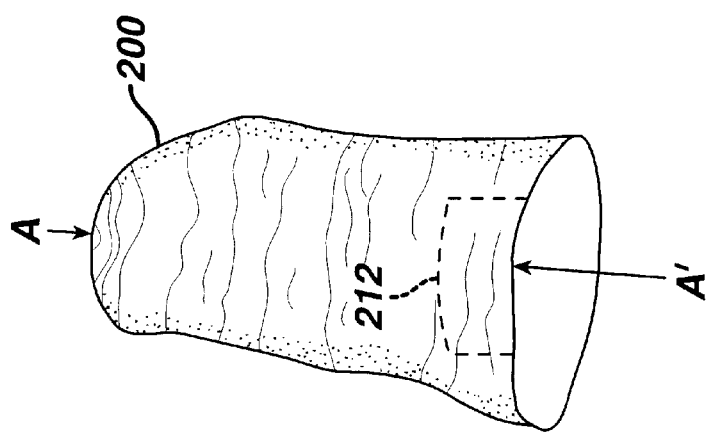
FIG. 15b
FIG. 15a

ACQUISITION, ANALYSIS AND DISPLAY OF ULTRASONIC DIAGNOSTIC CARDIAC IMAGES

This invention relates to ultrasonic diagnostic imaging systems and, in particular, to ultrasonic diagnostic imaging systems which automatically define the borders and boundaries of structures within an ultrasonic image.

Many ultrasonic diagnostic procedures in which bodily functions and structures are quantified rely upon clear delineation and definition of the body structures and organs which are being measured. When the quantification or measurement procedure uses static images or a small set of measurements, the delineation of the bodily structure being measured can be done manually. An example of such a procedure is the obstetrical measurements of a developing fetus. Static images of the developing fetus can be acquired during periods when fetal activity is low. Once an image is acquired, only a few circumference or length measurements are usually required to compute development characteristics such as gestational age and anticipated delivery date. These measurements can readily be made manually on the fetal images. Other diagnostic procedures, particularly those involving measurements of the heart and its functioning, present a further set of difficulties. The heart is always beating and hence is always in motion. As it moves, the contours of the heart constantly move and change as the organ contracts and expands. To fully assess many characteristics of cardiac function it is necessary to evaluate many and at times all of the images acquired during the heart cycle (one heartbeat), which can amount to thirty to one hundred and fifty or more images. The structure of interest such as the endocardium, epicardium or valves must then be delineated in each of these images, a painstaking, time-consuming task. Since these structures are constantly in motion, they appear slightly different in each image acquired during the cardiac cycle, and can also vary significantly from one patient to another. While applications such as obstetrical procedures would benefit from a processor which automatically delineates specific anatomy in an ultrasonic image, cardiac diagnosis would benefit even more so.

In order to be able to automatically delineate features in an image, it is necessary for the features to be clearly shown in the image. If the features are unclear the automatic process can fail, requiring user input for the delineation process or, worst of all, requiring the user to resort to a manual technique. It would be desirable for the user to be informed by the ultrasound system when images suitable for feature delineation are being acquired. Furthermore, it is desirable that images best suited for the intended diagnostic procedure be displayed and analyzed.

In accordance with the principles of the present invention, the end diastole and end systole images from an acquired cardiac loop are shown side by side on an image display for automatic border tracing. The cardiac loops may be first acquired then processed for automatic border definition, or the acquired images can be processed in real time to indicate their suitability for automatic border detection as they are acquired. The border tracings can be used to calculate ejection fraction in real time.

In the drawings:

FIG. 4 illustrates the step of locating the apex of the LV;

FIGS. 5a–5c illustrate standard border shapes for the LV;

FIGS. 15a–15c illustrate 3D techniques for evaluating cardiac performance;

Figure 1:
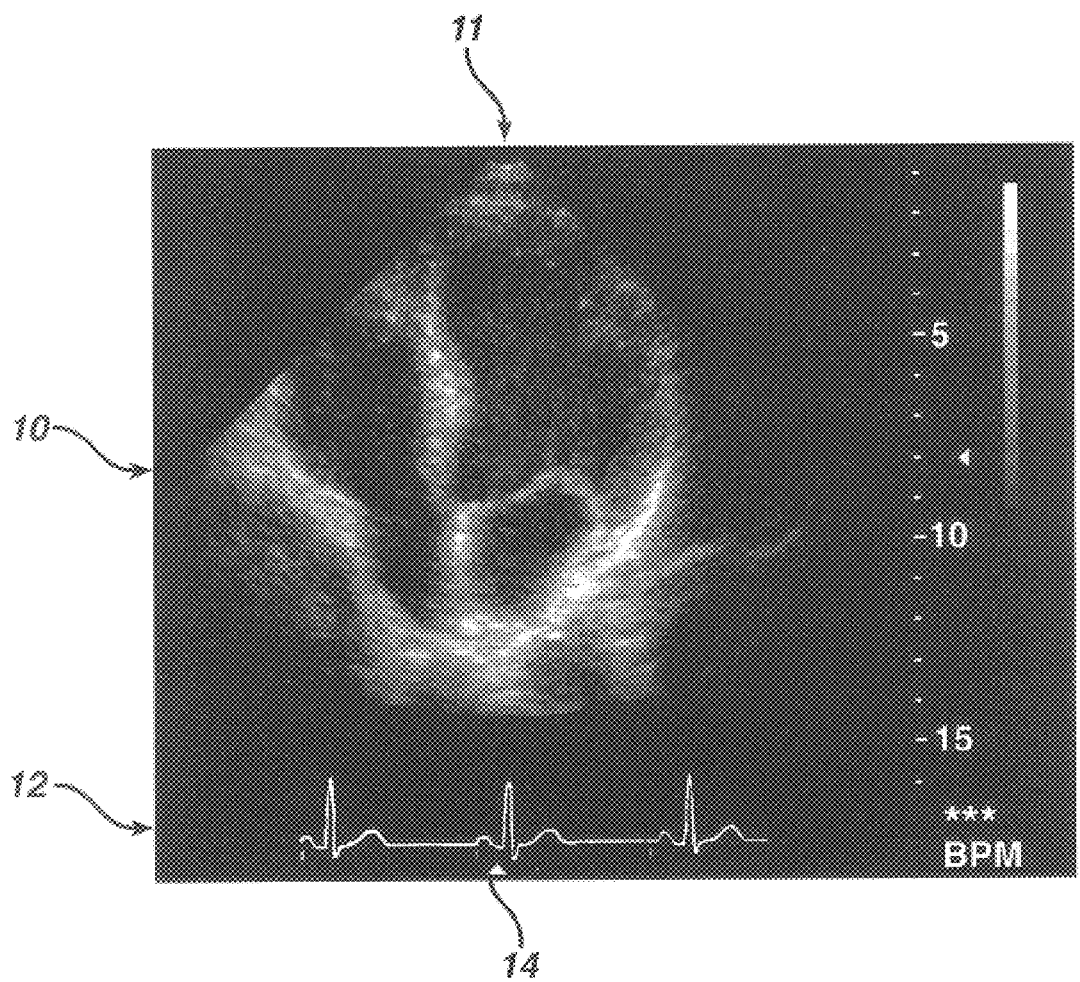
FIG. 1 is a four chamber ultrasound image of the heart.

Referring first to FIG. 1, an ultrasound system display is shown during the acquisition of cardiac images. The ultrasound image 10 is a four-chamber view of the heart which is acquired by a phased array transducer probe to produce the illustrated sector-shaped image. The image shown is one of a sequence of real-time images acquired by placement of the probe for an apical 4-chamber view of the heart, in which the probe is oriented to view the heart from the proximity of its apex 11. The largest chamber in the image, in the central and upper right portion of the image, is the left ventricle (LV). As the real-time ultrasound image sequence is acquired an ECG trace 12 of the heart cycle is simultaneously acquired and displayed at the bottom of the display, with a triangular marker 14 denoting the point or phase of the cardiac cycle at which the currently-displayed image was acquired. A typical duration of the heart cycle when the body is at rest is about one second, during which time approximately 30–90 image frames of the heart are acquired and displayed in rapid succession. A sequence of image frames for a heart cycle is referred to herein as a "looyp" of images, as a clinician will often acquire and save the sequence of images of a heart cycle and then replay them in a continuous "loop" which repetitively displays the selected cardiac cycle. As the clinician views the display of FIG. 1, the heart is seen beating in real time in the ultrasound display as the ECG waveform 12 scrolls beneath the ultrasound images 10, with the instantaneously displayed heart phase indicated by the marker 14.

In one mode of acquisition in accordance with the present invention, the clinician observes the beating heart in real time while manipulating the transducer probe so that the LV is being viewed distinctly in maximal cross-section. When the four chamber view is being acquired continuously and clearly, the clinician depresses the "freeze" button to retain the images of the current heart cycle in the image frame or Cineloop® memory of the ultrasound system. The Cineloop memory will retain all of the images in the memory at the time the freeze button is depressed which, depending upon the size of the memory, may include the loop being viewed at the time the button was depressed as well as images of a previous or subsequent loop. A typical Cineloop memory may hold 400 image frames, or images from about eight to ten heart cycles. The clinician can then scan through the stored images with a trackball, arrow key, or similar control to select the loop with the images best suited for analysis. When the clinician settles on a particular loop, the "ABD" protocol is actuated to start the border drawing process.

Figure 2:
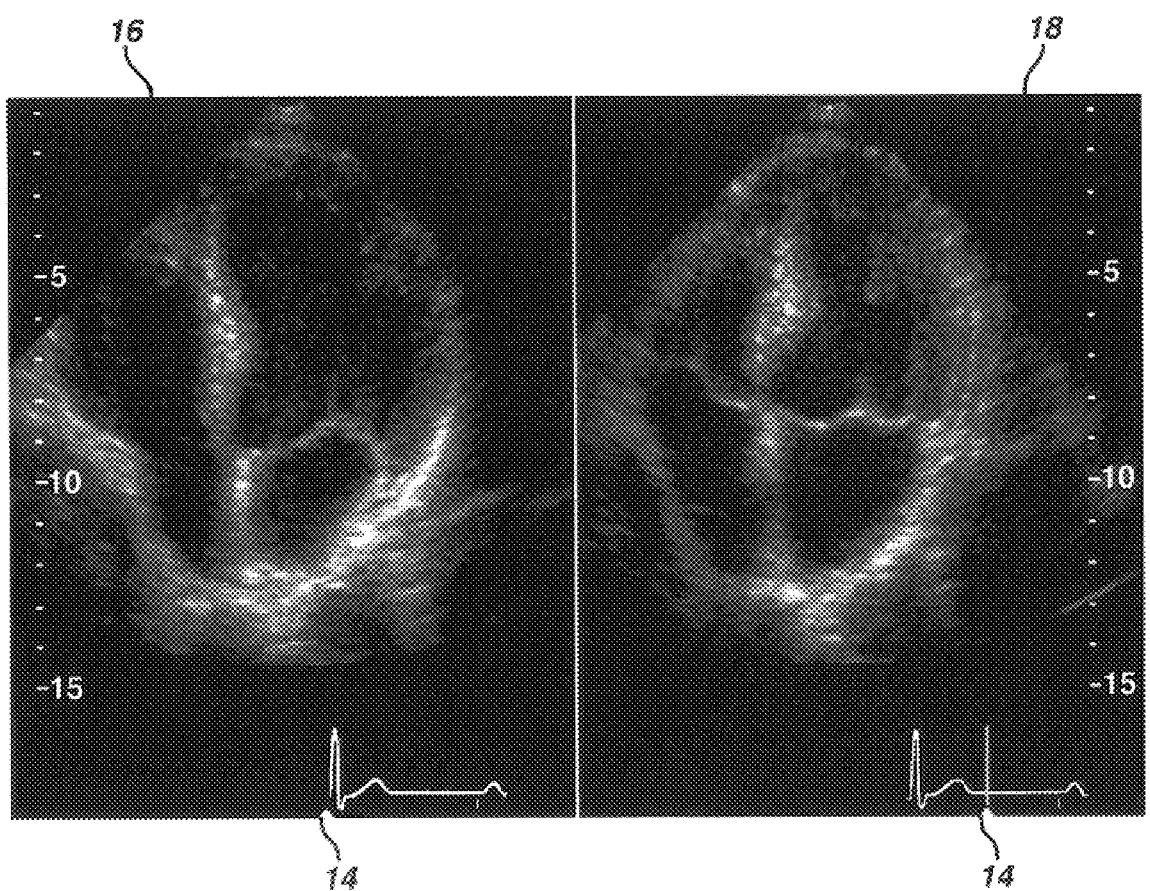
FIG. 2 illustrates an ultrasound display of both end diastole and end systole cardiac images.

When the ABD protocol is actuated the display changes to a dual display of the end diastole image 16 and the end systole image 18 displayed side-by-side as shown in FIG. 2. The ultrasound system identifies all of the images comprising the selected loop by the duration of the ECG waveform associated with the selected loop. The ultrasound system also recognizes the end diastole and end systole points of the cardiac cycle in relation to the R-wave of the ECG waveform 12 and thus uses the ECG waveform R-wave to identify and display the ultrasound images at these two phases of the heart cycle. The dual display of FIG. 2 shows the ECG waveform 12 for the selected heart cycle beneath each ultrasound image, with the marker 14 indicating the end diastole and end systole phases at which the two displayed images were acquired.

Since the Cineloop memory retains all of the images of the cardiac cycle, the user has the option to review all of the images in the loop, including those preceding and succeeding those shown in the dual display. For instance, the clinician can "click" on either of the images to select it, then can manipulate the trackball or other control to sequentially review the images which precede or succeed the one selected by the ultrasound system. Thus, the clinician can select an earlier or later end diastole or end systole image from those selected by the ultrasound system. When the clinician is satisfied with the displayed images 16 and 18, the ABD processor is actuated to automatically delineate the LV borders on the two displayed images as well as the intervening undisplayed images between end diastole and end systole.

Figure 3A:
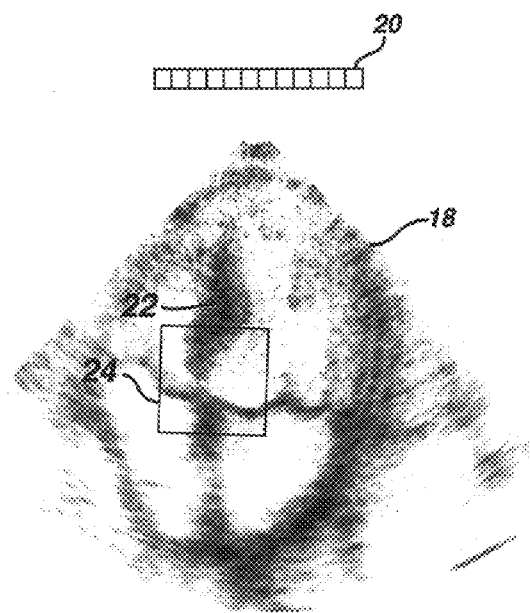
FIGS. 3a and 3b illustrate the step of locating the medial mitral annulus (MMA) and the lateral mitral annulus (LMA) in an ultrasound image of the left ventricle (LV)

In this example the ABD processor begins by drawing the endocardial border of the LV in the end systole image 18. The first step in drawing the border of the LV is to locate three key landmarks in the image, the medial mitral annulus (MMA), the lateral mitral annulus (LMA), and the endocardial apex. This process begins by defining a search area for the MMA as shown in FIG. 3a, in which the ultrasound image grayscale is reversed from white to black for ease of illustration. Since the ABD processor is preconditioned in this example to analyze four-chamber views of the heart with the transducer 20 viewing the heart from its apex, the processor expects the brightest vertical nearfield structure in the center of the image to be the septum which separates the left and right ventricles. This means that the column of pixels in the image with the greatest total brightness value should define the septum. With these cues the ABD processor locates the septum 22, and then defines an area in which the MMA should be identified. This area is defined from empirical knowledge of the approximate depth of the mitral valve from the transducer in an apical view of the heart. A search area such as that enclosed by the box 24 in FIG. 3a is defined in this manner.

Figure 6A:
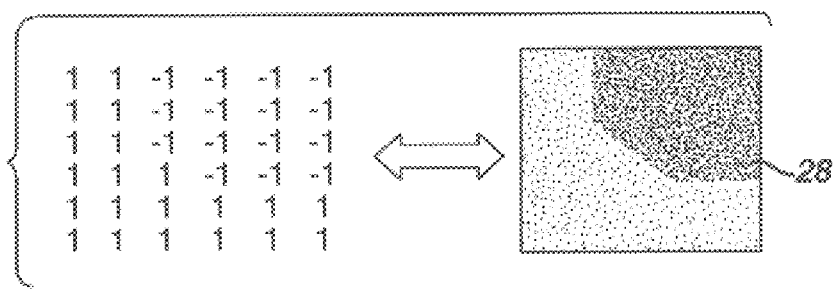
FIGS. 6a–6b illustrate geometric templates used to locate the MMA and LMA.

A filter template defining the anticipated shape of the MMA is then cross correlated to the pixels in the MMA search area. While this template may be created from expert knowledge of the appearance of the MMA in other four-chamber images as used by Wilson et al. in their paper "Automated analysis of echocardiographic apical 4-chamber images," *Proc. of SPIE*, August, 2000, the present inventors prefer to use a geometric corner template. While a right-angle corner template may be employed, in a constructed embodiment the present inventors use an octagon corner template 28 (the lower left corner of an octagon) as their search template for the MMA, as shown at the right side of FIG. 6a. In practice, the octagon template is represented by the binary matrix shown at the left side of FIG. 6a. The ABD processor performs template matching by cross correlating different sizes of this template with the pixel data in different translations and rotations until a maximum correlation coefficient above a predetermined threshold is found. To speed up the correlation process, the template matching may initially be performed on a reduced resolution form of the image, which highlights major structures and may be produced by decimating the original image resolution. When an initial match of the template is found, the resolution may be progressively restored to its original quality and the location of the MMA progressively refined by template matching at each resolution level.

Figure 3B:
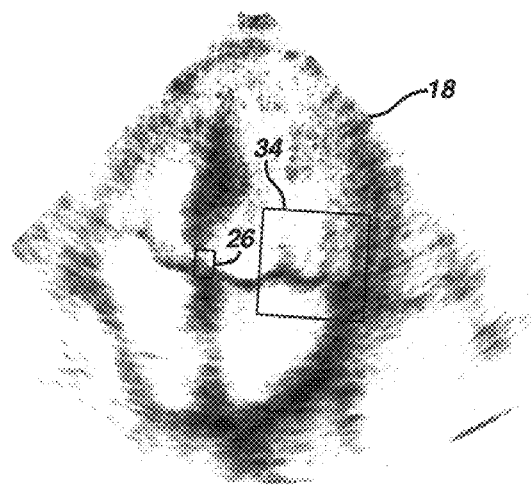
Figure 6B:
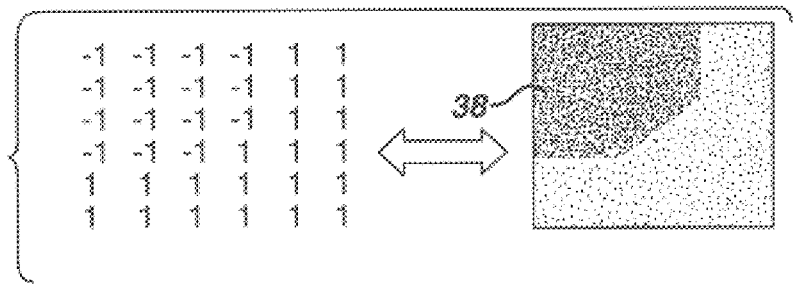

Once the MMA has been located a similar search is made for the location of the LMA, as shown in FIG. 3b. The small box 26 marks the location established for the MMA in the image 18, and a search area to the right of the MMA is defined as indicated by the box 34. A right corner geometric template, preferably a right octagon corner template 38 as shown in FIG. 6b, is matched by cross-correlation to the pixel values in the search area of box 34. Again, the image resolution may be decimated to speed the computational process and different template sizes may be used. The maximal correlation coefficient exceeding a predetermined threshold defines the location of the LMA.

Figure 7A:
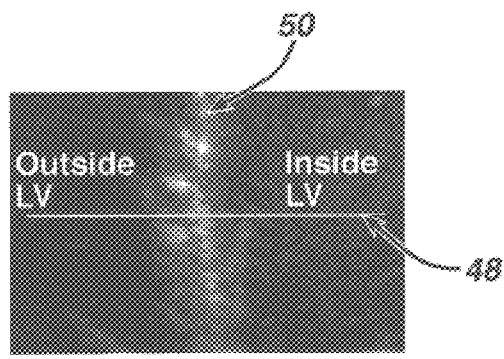
FIGS. 7a–7c illustrate a technique for fitting a standard border shape to the endocardial boundary of the LV.
Figure 7B:
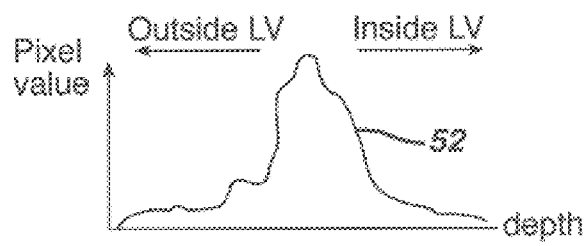
Figure 7C:
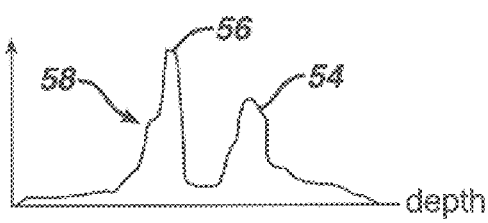

With the MMA 26 and the LMA 36 found, the next step in the process is to determine the position of the endocardial apex, which may be determined as shown in FIG. 4. The pixel values of the upper half of the septum 22 are analyzed to identify the nominal angle of the upper half of the septum, as indicated by the broken line 43. The pixel values of the lateral wall 42 of the LV are analyzed to identify the nominal angle of the upper half of the lateral wall 42, as shown by the broken line 45. If the lateral wall angle cannot be found with confidence, the angle of the scanlines on the right side of the sector is used. The angle between the broken lines 43, 45 is bisected by a line 48, and the apex is initially assumed to be located at some point on this line. With the horizontal coordinate of the apex defined by line 48, a search is made of the slope of pixel intensity changes along the line 48 to determine the vertical coordinate of the apex. This search is made over a portion of line 48 which is at least a minimum depth and not greater than a maximum depth from the transducer probe, approximately the upper one-quarter of the length of line 48 above the mitral valve plane between the MMA 26 and the LMA 36. Lines of pixels along the line 48 and parallel thereto are examined to find the maximum positive brightness gradient from the LV chamber (where there are substantially no specular reflectors) to the heart wall (where many reflectors are located). A preferred technique for finding this gradient is illustrated in FIG. 7. FIG. 7a shows a portion of an ultrasound image including a section of the heart wall 50 represented by the brighter pixels in the image. Drawn normal to the heart wall 50 is a line 48 which, from right to left, extends from the chamber of the LV into and through the heart wall 50. If the pixel values along line 48 are plotted graphically, they would appear as shown by curve 52 in FIG. 7b, in which brighter pixels have greater pixel values. The location of the endocardium is not the peak of the curve 52, which is in the vicinity of the center of the heart wall, but relates to the sense of the slope of the curve. The slope of the curve 52 is therefore analyzed by computing the differential of the curve 52 as shown by the curve 58 in FIG. 7c. This differential curve has a peak 56 which is the maximal negative slope at the outside of the heart wall (the epicardium). The peak 54, which is the first major peak encountered when proceeding from right to left along curve 58, is the maximal positive slope which is the approximate location of the endocardium. The pixels along and parallel to line 48 in FIG. 4 are analyzed in this manner to find the endocardial wall and hence the location of the endocardial apex, marked by the small box 46 in FIG. 4.

Once these three major landmarks of the LV have been located, one of a number of predetermined standard shapes for the LV is fitted to the three landmarks and the endocardial wall. Three such standard shapes are shown in FIGS. 5a, 5b, and 5c. The first shape, border 62, is seen to be relatively tall and curved to the left. The second shape, border 64, is seen to be relatively short and rounded. The third shape, border 66, is more triangular. Each of these standard shapes is scaled appropriately to fit the three landmarks 26, 36, 46. After an appropriately scaled standard shape is fit to the three landmarks, an analysis is made of the degree to which the shape fits the border in the echo data. This may be done, for example, by measuring the distances between the shape and the heart wall at points along the shape. Such measurements are made along paths orthogonal to the shape and extending from points along the shape. The heart wall may be detected using the operation discussed in FIGS. 7a–7c, for instance. The shape which is assessed as having the closest fit to the border to be traced, by an average of the distance measurements, for instance, is chosen as the shape used in the continuation of the protocol.

The chosen shape is then fitted to the border to be traced by "stretching" the shape, in this example, to the endocardial wall. The stretching is done by analyzing 48 lines of pixels evenly spaced around the border and approximately normal to heart wall. The pixels along each of the 48 lines are analyzed as shown in FIGS. 7a–7c to find the adjacent endocardial wall and the chosen shape is stretched to fit the endocardial wall. The baseline between points 26 and 36 is not fit to the shape but is left as a straight line, as this is the nominal plane of the mitral valve. When the shape has been fit to points along the heart wall, the border tracing is smoothed and displayed over the end systole image as shown in the image 78 on the right side of the dual display of FIG. 8. The display includes five control points shown as X's along the border between the MMA landmark and the apex, and five control points also shown as X's along the border between the apex landmark and the LMA landmark. In this example the portion of line 48 between the apex and the mitral valve plane is also shown, as adjusted by the stretching operation.

With the end systole border drawn in this manner the ABD processor now proceeds to determine the end diastole border. It does so, not by repeating this operation on the end diastole image 16, but by finding a border on each intervening image in sequence between end systole and end diastole. In a given image sequence this may comprise 20–30 image frames. Since this is the reverse of the sequence in which the images were acquired, there will only be incremental changes in the endocardial border location from one image to the next. It is therefore to be expected that there will be a relatively high correlation between successive images. Hence, the end systole border is used as the starting location to find the border for the previous image, the border thus found for the previous image is used as the starting location to find the border for the next previous image, and so forth. In a constructed embodiment this is done by saving a small portion of the end systole image around the MMA and the LMA and using this image portion as a template to correlate and match with the immediately previous image to find the MMA and the LMA locations in the immediately previous image. The apex is located as before, by bisecting the angle between the upper portions of the septum and lateral LV wall, then locating the endocardium by the maximum slope of the brightness gradient. Since the LV is expanding when proceeding from systole to diastole, confidence measures include the displacement of the landmark points in an outward direction from frame to frame. When the three landmark points are found in a frame, the appropriately scaled standard shape is fit to the three points. Another confidence measure is distention of the standard shapes; if a drawn LV border departs too far from a standard shape, the process is aborted.

Border delineation continues in this manner until the end diastole image is processed and its endocardial border defined. The dual display then appears as shown in FIG. 8, with endocardial borders drawn on both the end diastole and end systole images 76, 78.

Figure 8:
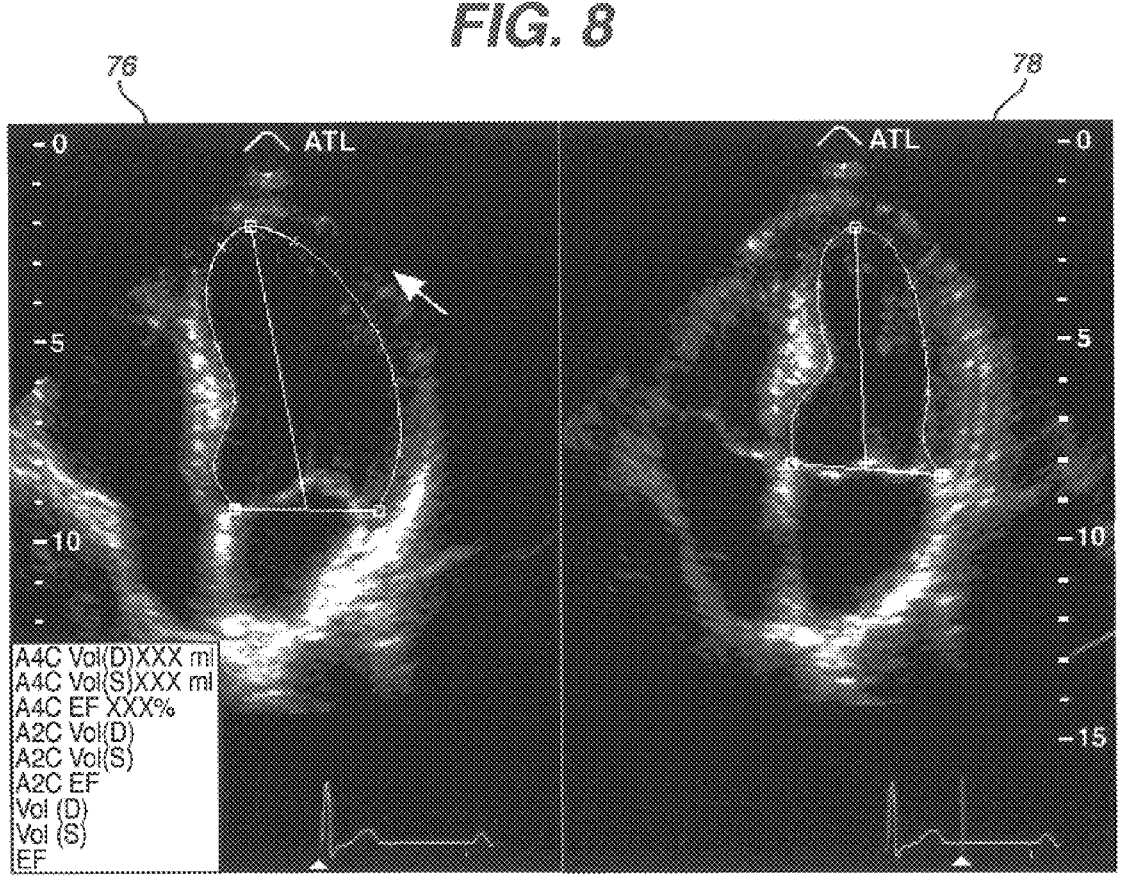
FIG. 8 illustrates an end diastole and end systole display with endocardial borders drawn automatically in accordance with the principles of the present invention.
Figure 9:
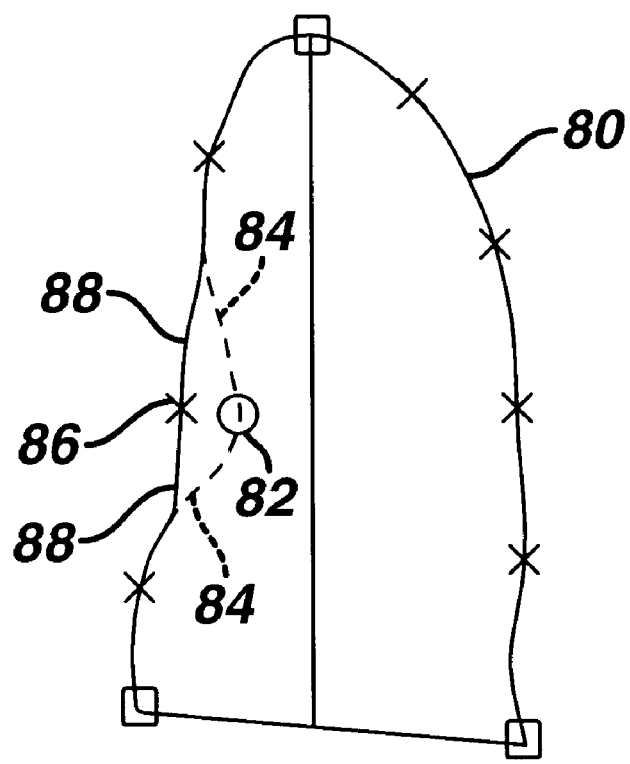
FIG. 9 illustrates the rubber-banding technique for adjusting an automatically drawn border.

As FIG. 8 shows, the endocardial borders of both the end diastole and end systole images have small boxes denoting the three major landmarks and control points marked by X's on the septal and lateral borders. The clinician chooses the default number of control point which will be displayed initially; on the border 80 shown in FIG. 9 there are three control points shown on the septal wall and four control points shown on the lateral wall. The clinician can review the end diastole and systole images, as well as all of the intervening images of the loop if desired, and manually adjust the positions of the landmark boxes and control point X's if it is seen that the automated process placed a border in an incorrect position. The clinician can slide a box or X along the border to a new position, and can add more control points or delete control points from the border. The process by which the clinician relocates a box or X laterally is known as rubberbanding. Suppose that the ABD processor had initially located the control point and border at the position shown by circle 82 and dashed line 84, which the clinician observes is incorrect. The clinician can relocate the control point laterally by dragging the X with a screen pointing device to the new location as shown by 86. As the X is dragged, the border moves or stretches along with the X, thereby defining a new border as shown by the solid line border 88. In this manner the clinician can manually correct and adjust the borders drawn by the ABD processor. As the clinician laterally relocates a control point X, the ABD processor responds by automatically recalculating the positions of the adjoining border and adjacent control points if necessary so that the border remains smoothly continuous. The recalculation will not adjust the position of a control point or landmark box which has been previously manually repositioned by the clinician, thereby preserving this expert input into the border drawing process. If the clinician relocates a landmark box, the ABD processor recalculates and refits the entire border to the landmarks and heart wall. Since the adjustment of one border in the image sequence can affect the borders of temporally adjacent images in the sequence, the ABD processor will also respond to a manual adjustment by correlating the adjusted border with temporally adjacent borders so that the manual adjustment is properly continuously represented in some or all of the images in the loop.

Another way to interactively adjust the drawn borders is to assemble only the border tracings in a "stack" in time sequence from ED to ES or later to form a surface defined by the borders which is viewed in three dimensions such as in a kinetic parallax display. The continuous surface formed by the borders can be assessed and adjusted as desired by a rubberbanding technique know as active surface adjustment. If the clinician sees a point on the surface formed by the borders which is out of alignment with temporally adjacent tracings or the desired border, the clinician can pull or push on the surface with a pointing device. The active surface adjustment then conforms the adjacent borders and the surface defined thereby to the adjustment made by the clinician, much as a balloon conforms when depressed at a point on its surface. The clinician can thus observe the effect of an adjustment made to one border on the temporally surrounding borders of the cardiac cycle.

In a preferred embodiment the control points are not simply distributed at uniform intervals around the drawn border, but their positions correspond to constant anatomical locations from frame to frame over the heart cycle. This may be done by referencing the control points of the image to those of a reference image through speckle tracking, feature tracking, or any kind of vector velocity or displacement processing. Since points in anatomy shown in an ultrasound image will exhibit a substantially constant pattern of speckle from frame to frame, the control points in other images can be located at points on their respective drawn borders which correspond to their characteristic speckle locations on the reference image. When the control points are located at constant anatomical positions they will appear to move closer together and then further apart through the heart cycle as the heart wall contracts and expands. When a control point X is relocated on a border by the clinician, the corresponding control point X's on the other images are correspondingly relocated automatically to the new speckle-tracked locations on each image. Such constant anatomical locations for the control points are important when assessing local heart wall motion as discussed below.

Since each of the images shown in FIG. 8 is one image in the cardiac loop of images, the clinician can further verify the accuracy of the borders of the end diastole and end systole images 76, 78 by playing the cardiac loop of images behind the borders drawn on the display of FIG. 8. This is done by selecting one of the images of FIG. 8, then selecting "Play" from the system menu to repetitively play the cardiac loop in real time or at a selected frame rate of display behind the border. In the end diastole image 76 the endocardium is at its maximum expansion; hence, the endocardium in the loop should appear to move inward from and then back to the endocardial border drawn on the end diastole image. In the end systole image 78 the endocardium is fully contracted; hence, the endocardium in the loop should appear to move outward and then back to the border in this image. If the endocardium does not move in this manner and, for example, is seen to pass through the border, a different image may need to be chosen for end diastole or end systole, or manual adjustment of a drawn border may be necessary. Of course, the loop and its drawn borders over the complete cardiac cycle can be replayed, enabling the clinician to view to endocardial tracing as it changes with the heart motion in real time.

As the ABD processor is identifying the key landmarks and fitting borders to the sequence of images, it is periodically making confidence measurements to gauge the likelihood that the image borders are being accurately located and traced. For instance, if the septum is not clearly contrasted from the blood pool in the LV chamber, the automated process will stop. If the various correlation coefficients do not exceed predetermined thresholds the process will stop. Both spatial and temporal confidence measurements are employed. For instance, if the computed border of an image varies too much from a standard shape in either size or shape, the process will abort. This can arise if the landmarks are located in unusual positions in relation to each other, for example. If the change in the computed border from one image in the sequence to another is too great, the process will likewise abort. When the process stops, a message is displayed notifying the clinician of the reason for stopping the process, and gives the clinician the option to continue the automated process, to continue the automated process with or after clinician input, or for the clinician to acquire a new loop of images or manually trace the current images.

In the illustrated example of FIG. 8 the automatically drawn borders of the end diastole and end systole images are used to compute the heart's ejection fraction. This is done by an automatic modified Simpson's rule process which divides the delineated heart chamber at each phase into a stack of virtual disks. The diameter of each disk is used with the disk height to compute an effective volume of each disk, and these volumes are summed to compute the heart chamber volume at both end diastole and end systole. The difference between the two yields the ejection fraction, the volume or percentage of the heart volume which is expelled as pumped blood during each heart cycle. The ejection fraction calculation is shown in the measurement box at the lower left hand corner of FIG. 8 and is constantly updated. Thus, if the clinician should adjust a drawn border by the rubberbanding technique, the computed volume of the heart during that phase will change, affecting the ejection fraction calculation, and the new calculation immediately appears in the measurement box. As the clinician adjusts the drawn borders he instantaneously sees the effects of these changes on the calculation of the ejection fraction.

Figure 10:
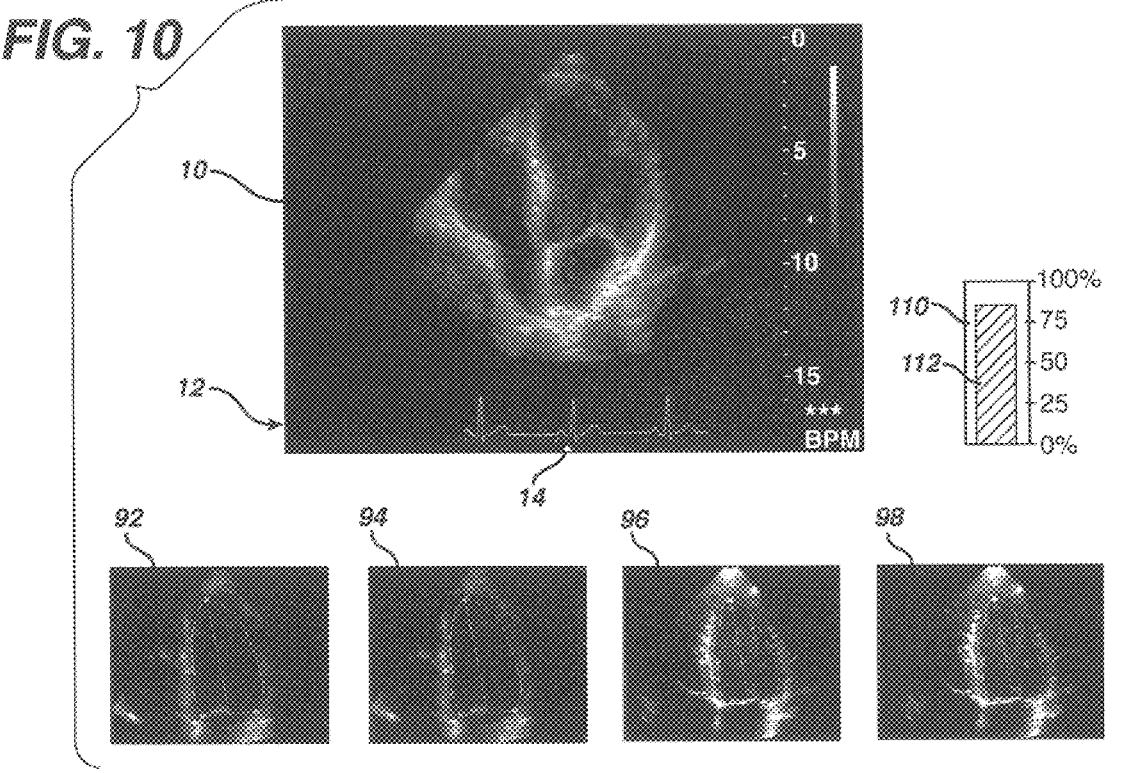
FIG. 10 illustrates the selection of a cardiac cycle by viewing automatically drawn borders.

In the previous example the clinician began by acquiring a cardiac loop on which to automatically trace borders. FIG. 10 shows an ultrasound image display in which a loop is acquired based upon the ability of the ABD processor to automatically draw borders on the images. In the illustrated display the real time ultrasound image 10 is continuously viewed as in FIG. 1 as the clinician manipulates the transducer probe to acquire the desired four chamber view of the heart. As the clinician manipulates the probe the ABD processor is operative to attempt to draw borders on at least one of the images of each cardiac cycle. Using the R-wave timing of the ECG trace 12, the ultrasound system automatically selects the image or images to be traced from each loop. The selected image could be the first image of a cardiac cycle, the end diastole image, or the end systole image, for instance. As the ABD processor attempts to draw borders on the fly on the selected images of the real time loops, the results of the ABD process for an image of each loop is shown as a small "thumbnail" image 92–98 below the real time image 10. In the illustrated example four thumbnail images are shown for four consecutive loops. Each time a new thumbnail is processed by the ABD processor it appears at the right side of the row of thumbnail images, the oldest thumbnail image disappears, and the row slides to the left. Initially the clinician may not be acquiring the heart in an orientation which is acceptable for the ABD process, at which time the progression of thumbnail images will show no borders as the ABD processor is unable to successfully draw borders on the images. But as the clinician manipulates the probe to acquire the necessary viewing plane for successful ABD performance and the images are acquired with better clarity and definition, borders will appear on the progression of thumbnail images as shown in the drawing figure. When the clinician is holding the probe at the necessary angulation relative to the heart so that the ABD process is continuously successful, the progression of thumbnail images will continuously show successfully drawn borders. The clinician will then freeze the acquisition to capture one or more of the successfully traced loops in the Cineloop memory, and will then select one of the loops for full ABD processing and display as described above. Thus, the ABD processor is used to assist the clinician in manipulating the probe for successful image acquisition and in acquiring loops which can be successfully processed for border definition by the ABD processor.

Another way to indicate to the clinician that acceptable images for ABD processing are being acquired is by means of a graphical ABD success indicator. Such an indicator may be qualitative, quantitative, or both, as is the example shown in FIG. 10. At the right of the display of FIG. 10 is a gauge 110 which is quantified from zero to 100%. When the clinician is acquiring images which are unsuitable for ABD processing, the gauge 110 is empty. But as suitable images begin to be acquired, a color bar 112 begins to rise from the bottom of the gauge. The quantization of the gauge indicates either the percentage of borders which were attempted and successfully drawn, or the changes in overall confidence measures as discussed above. In the drawing a green bar is at the 80% level, indicating that the ABD processor was able to successfully process 80% of the images attempted over a recent interval such as the last few heart cycles, or that the borders drawn achieved an 80% confidence level of accuracy.

A third way to indicate ABD success to the clinician is to present drawn borders in real time on the real time images 10. The ABD processor can attempt to draw a border on a single image for each heart cycle, such as the end systole image, and the successfully drawn border is displayed over the real time image for the duration of that heart cycle until the time of the next end systole image. Alternatively, if sufficient processing speed is available, borders are calculated and displayed for every image in the heart cycle. In either case, the drawn border will not appear or will flicker on and off when unsuitable or marginal cardiac images are being acquired, but will constantly appear when a succession of suitable images is being acquired, at which time the clinician knows that the probe is oriented to acquire good four chamber views for ABD processing.

In addition to the LV of four chamber views, the ABD processor of the present invention can also define borders in other types of ultrasound images. Short axis views can be processed for automatic border definition, in which case the landmarks used can be the annulus or the outflow track. Alternatively, the center of the heart chamber can be found from its contrast with the surrounding heart wall, then the desired border located by radial extension and fitting of a circular standard shape. The walls of blood vessels such as the carotid artery can similarly be traced by identifying the center line of the vessel, then extending straight line shapes out from opposite sides of the center line to fit small line segments to the endothelial wall. Fetal anatomy such as the fetal cranium can also be automatically traced by use of an elliptical shape.

Figure 11:
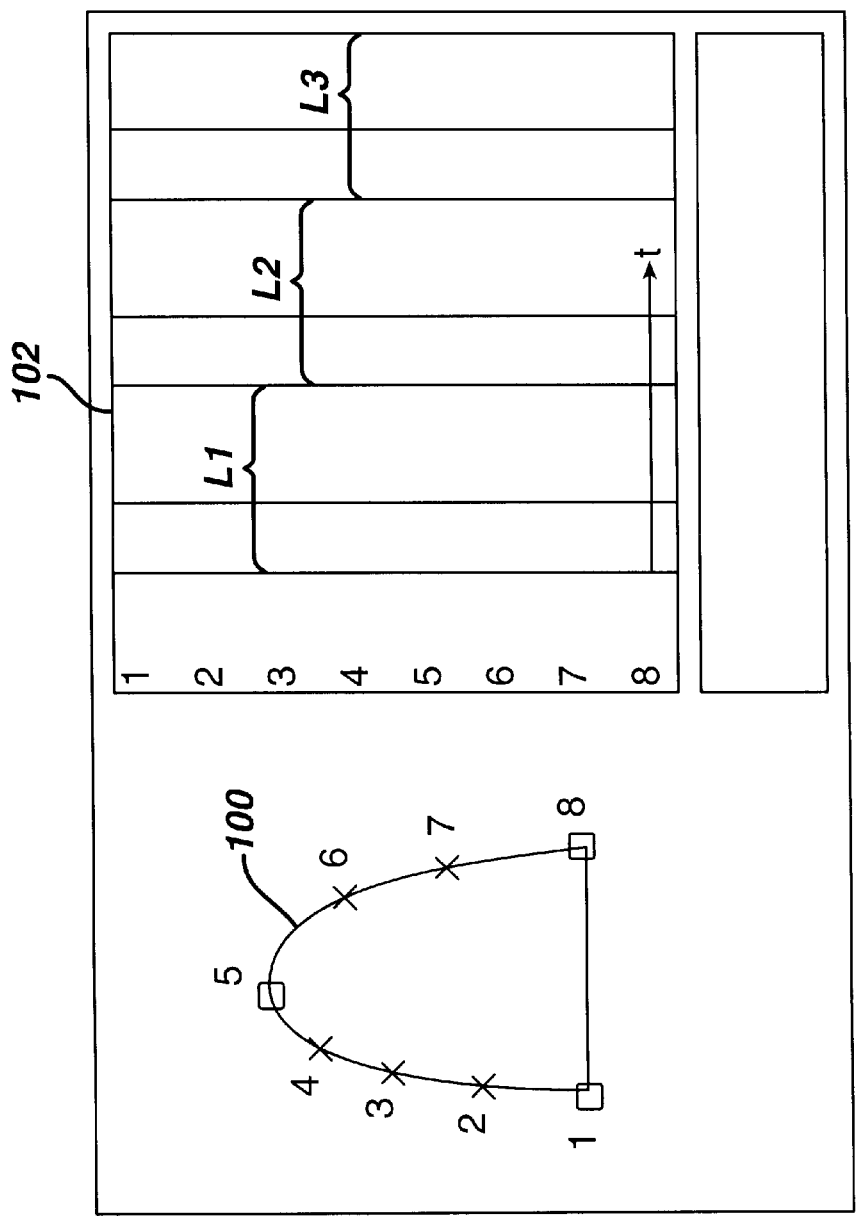
FIG. 11 illustrates a tissue Doppler map of endocardial motion over a plurality of cardiac cycles.

With the ability to automatically draw borders of structures of the heart such as the endocardium on a complete loop of images, a number of diagnostic techniques become practical. For instance, FIG. 11 illustrates a technique for assessing regional wall motion using automated border detection. The drawing of FIG. 11 represents an ultrasound display in which the continuous motion of the endocardium or myocardium is shown over several complete heart cycles. The ABD processor is operated as described above to draw a trace along the endocardial border or continuously through the myocardium of the images of one or more loops. The latter is performed by tracing the endocardial border as described above, then drawing a curve parallel to and slightly larger than the endocardial border curve. Such a curve will reliably pass continuously through the heart muscle. The border 100 for one such image is shown at the left side of the drawing, with the landmark points and control points numbered from one to eight in sequence around the border. For analysis of wall motion the image points beneath the border are Doppler processed to determine the velocity, Doppler power or variance along the defined border. Thus, a tissue Doppler image line is computed along the endocardium or myocardium at locations defined by the automatically drawn border. This Doppler processing is performed for the defined border of each image in the loop or loops. The Doppler processed information from the moving tissue may be fundamental frequency signals or harmonic frequency signals which can be processed as described in U.S. Pat. No. 6,036,643. The lines of Doppler values for all of the images are displayed in straight vertical lines as shown at the right side of FIG. 11 as indicated by the vertical sequence of numbers 1–8. The lines are arrayed sequentially adjacent to each other in the time sequence of the images. The Doppler values are preferably displayed in color, thus forming a color M-mode display area 102. The display in area 102 may be referred to as an ABD-TDI (ABD with tissue Doppler imaging) display. In the illustrated display the color Doppler lines for the first loop are arrayed across the area indicated by bracket L, the color Doppler lines for the next loop are arrayed across the area indicated by bracket L2, and the color Doppler lines for the third loop are arrayed across the area indicated by bracket L3, and so on. As the arrow at the bottom of the display area 102 indicates, the Doppler lines progress in time in the horizontal direction. This display 102 thus shows in a continuum over the heart cycle the motion of the LV myocardium. This display enables the clinician to follow the motion of one point or region of the heart wall over a full cardiac cycle by observing a horizontal row of the display. For instance, the heart wall at the apex of the heart is marked by 5 at the left of the area 102, corresponding to the apex landmark 5 on the border 100. By viewing the Doppler data (colors) to the right of 5 in area 102 the clinician is able to see the velocity or change in velocity or intensity of motion of the heart wall at the apex of the heart as it varies over the complete heart cycle or cycles. If a region of the wall is not moving due to infarction or some other defect, it can be spotted by a change or difference in color at a particular horizontal elevation in the ABD-TDI display.

It will be appreciated that, since the LV heart wall is constantly expanding and contracting as the heart beats, the length of the line 100 from the MMA, around the apex, and back to the LMA is constantly changing in correspondence. If the control points are simply delineated in even spacings around the line 100, they may not continuously correspond to the same points of the heart wall through the full heart cycle. This is overcome by tracking the anatomy from a baseline of control points over the heart cycle, as by speckle tracking each local point of the heart wall along the ABD trace from frame to frame, as described above. The different length lines are rescaled or normalized to a common length so that a horizontal line extended to the right from each number at the left of the display 102 will relate to the same point or region of the heart wall over the continuum of tissue Doppler lines.

An ABD-TDI display may also be formed from short axis images of the heart. In short axis views the heart wall exhibits a ring shape. As described previously, the endocardium can be traced automatically for each frame of the cardiac cycle and a parallel, slightly larger circle than the tracing can be drawn through the myocardial muscle in the images. Doppler values are acquired around each of these circles, which are displayed in a continuum of lines in the format shown in area 102 of FIG. 11. Thus, the display format 102 may be used for either short or long axis views of the heart.

Figure 12:
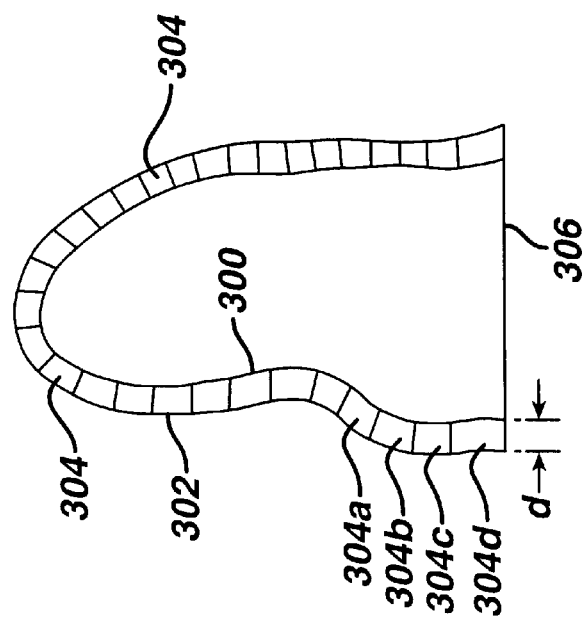
FIG. 12 illustrates the use of automated border detection to segment an image of the heart wall.

Another application for automatically drawn cardiac borders is shown in FIG. 12. In this illustration the border 300 represents the endocardial border defined by automated border detection as described above, with a line 306 for the mitral valve plane at the bottom. A second, slightly larger border 302 is drawn around the first border 300. This second border may be an ABD-produced border of the epicardium, or it may be a trace spaced by a predetermined lateral distance d normal to the endocardial border 300. In this latter case, the trace 302 can pass continuously through the myocardium. Thus, Doppler values along the trace 302 would yield motional measures taken in a central portion of the heart muscle. The space between the two traces can be divided into small areas 304 and the Doppler values within each area integrated to produce a measure of regional wall motion at a particular location on the LV wall. These measures are made using ABD processing of many or all of the images of the cardiac loop to quickly and accurately provide quantified measures of cardiac performance over most or all of the cardiac cycle.

Figure 13A:
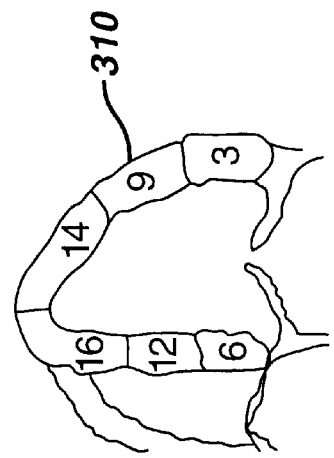
FIGS. 13a and 13b illustrate scorecards for scoring segments of the heart wall.
Figure 13B:
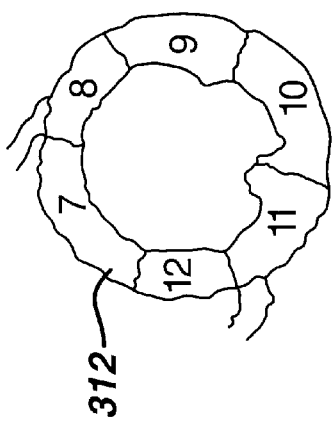

The measurements made from the areas 304 can be used to automatically fill out an anatomically corresponding scorecard for cardiac performance. For example, FIG. 13a shows a graphical representation 310 of the LV in a 4-chamber view, with the myocardium divided into numbered areas. The region numbered 6 on the anatomical scorecard 310 corresponds to the small areas 304a–304d which were defined by automatically drawn borders. The measurements taken in these areas 304a–304d can be aggregated and used to automatically place a score on the scorecard 310 for region 6, which may be numerical or qualitative, for example, a coded color. The score can be a peak or average value measured for one phase of the heart cycle or taken over all the frames of the full heart cycle. FIG. 13b illustrates a similar anatomical scorecard 312 for a short axis view of the heart, which may be used to score images with automatically drawn borders acquired from that view. A scorecard may be filled in for just a single image frame, for a group of image frames taken together, or a scorecard may be completed for each frame of a cardiac sequence. In the latter case, color coded scorecards can be played in rapid succession in a real time (or slower or faster) loop of images of the scorecards, enabling the clinician to view the time variation of a region of the heart in a segment of the scorecard which is stationary on the display screen from frame to frame.

Automatically drawn cardiac borders may also be used to define the myocardial area in contrast-enhanced images or loops. The addition of a contrast agent to the cardiac imaging exam allows the physician to assess how well the heart muscle is being perfused with blood. Automatically computed borders may be used as input into a variety of perfusion quantification algorithms. Automatically drawn cardiac borders and perfusion information presented simultaneously in an image or loop is a powerful combination since the clinician can assess wall motion, thickening, and perfusion simultaneously. Given that the borders are known, the thickness of the myocardial walls between the endocardial and epicardial edges can be determined on a segment-by-segment basis as shown in FIG. 12. Perfusion information quantified by an independent algorithm may also be displayed side-by-side with the quantitative wall thickening information. Quantitative perfusion information and wall thickening nay also be parametrically combined and presented on a segment-by-segment basis in a color coded display for Doppler and wall motion integration.

Another diagnostic technique made practical by automatic border detection is strain rate analysis of cardiac performance. The strain rate is a measurement computed as the axial derivative of the velocity of the tissue, and can lead to a representation of the relative deformation of the tissue during contraction or expansion. The conventional way to compute strain rate in an ultrasound image is to find Doppler velocity values along the ultrasound beams, then to compute the spatial gradient as a derivative using successive velocity values along the beam. This spatial gradient of velocity is thus strongly dependent upon the variable relationship between the beam directions and the anatomy in the image, which means that the strain rate values can change as the probe is moved. The present inventors prefer to use a strain rate calculation which is dependent upon the direction of tissue motion rather than an arbitrary beam direction. Accordingly the present inventors calculate strain rate in the direction of the velocity vector of tissue motion. In order to do this it is necessary to have not only velocity values for the tissue pixels in an image but also the direction or vectorial component of the motion, which can be obtained by known vector Doppler techniques. The differential between adjacent pixels in the direction of motion is then computed as the strain rate. The strain rate can be computed from fundamental frequency echo information, or from harmonic frequency signals which can be more clutter-free than the fundamental frequency signals.

Figure 14B:
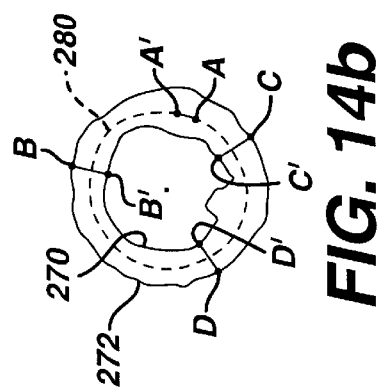
FIGS. 14a and 14b illustrate techniques for making strain rate measurements as a function of tissue motion.
Figure 14A:
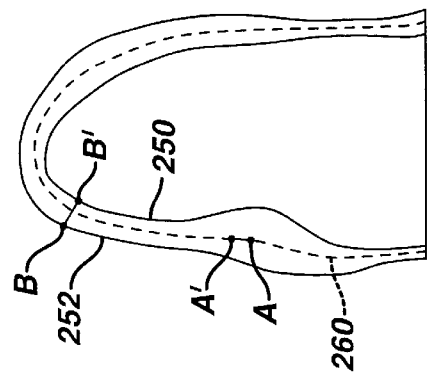

FIG. 14a shows two traces which have been automatically drawn over the borders of a 4-chamber view of the LV. The border 250 is drawn to define the endocardium and the border 252 has been drawn to define the epicardium of the LV. A third trace 260 is automatically drawn between the endocardial and epicardial borders. This third trace 260 will reliably pass continuously through the myocardium. These traces enable the strain rate to be computed for the two major components of motion of the LV. One of these components is the contraction and expansion of adjoining cells in the heart muscle. This motion is generally along the direction of the trace 260. A strain rate representation of this cellular motion can be found by differentiating the velocity values of successive points A–A' along trace 260 as shown in the drawing. The overall motion of the heart chamber as the muscle cells contract and expand is toward and away from the center of the heart chamber. A strain rate representation of this second motional component is computed by differentiating velocities in a direction normal to the drawn borders such as at points B–B' across the heart muscle. The strain rate so calculated along the myocardium is preferably displayed in a color-coded representation. A similar set of strain rate measurements can be made using borders 270 (endocardium) 272 (epicardium) and trace 280 (myocardium) drawn on short axis views of the heart such as that shown in FIG. 14b. In that drawing muscle cell contraction and expansion is used to compute strain rate in the circumferential direction such as would be computed from the velocities at points A–A' in the image. Radial components of expansion and contraction are represented in a strain rate display by differentiating in the radial direction such as by using the velocities at points B–B', C–C', and D–D'. The strain rate over the full cardiac cycle can be displayed by computing the strain rate around the entire border for each frame in the cardiac cycle, then displaying the strain for each frame as a vertical line in a time sequence of lines as shown by display 102 in FIG. 11.

FIGS. 15*a* and 15*b* illustrate the use of automated border detection in three dimensional imaging. The previous examples have shown how borders can be automatically drawn on two dimensional cardiac images. The technique described above is effective for defining the borders of three dimensional cardiac images also. If a three dimensional cardiac image is produced by acquiring a series of spatially adjacent 2D image planes of the heart, the ABD process described above can be performed on each component frame to define a series of boundaries which together define a surface of the heart such as the endocardial surface. If the three dimensional cardiac image is produced from ultrasonic beams steered in three dimensions to scan the heart three dimensionally in real time as described in U.S. patent application Ser. No. 09/645,872 entitled "ULTRASONIC DIAGNOSTIC IMAGING OF THE CORONARY ARTERIES," the resulting three dimensional data set can be divided into a series of parallel planes which are processed as described above to define a series of planar borders which can be assembled to provide a boundary such as the heart wall. Preferably the three dimensional data set is processed three dimensionally, in which case advantage is taken of the contiguous nature of the heart wall in three dimensions in the data set to more reliably define the three dimensional border In either case, the resultant three dimensional border of the LV endocardium may appear as shown in FIG. 15*a*, a somewhat elongated pouch-like surface which is closed at the apex end A and open at the mitral valve plane A'. FIG. 15*a* represents the three dimensional endocardial surface traced at one phase of the heart cycle. In each 3D image of a 3D cardiac loop the endocardial surface will be slightly different as the LV continuously contracts and expands during the heart cycle. Thus a different border surface 200 can be computed for each three dimensional image in the loop. Since the speed of sound may not enable the ultrasonic data for a full 3D image to be acquired at the desired 3D frame rate, the 3D images may be built up over time by using a heart gate triggered from the ECG waveform to acquire the data for a portion of a 3D image at specific phases of the heart over numerous cardiac cycles until the full data set necessary to produce 3D images of the desired temporal spacing over the entire heart cycle is acquired.

The 3D image of the endocardium in FIG. 15*a* can be produced by Doppler processing, thereby revealing the velocity, variance, or Doppler power at each point on the LV wall by rotating and examining the endocardial tissue Doppler surface 200. Another way to view the Doppler information for the entire endocardium is to "unwrap" the tissue Doppler surface 200 to a two dimensional form as shown in FIG. 15*b*. In this illustration the apex is located at A and the mitral valve plane extends along the bottom edge between A' and A'. In this display the clinician can examine the motion of the entire endocardium in one view. Such a display shows motion at only one phase of the heart cycle, the phase indicated by cursor 14 below the ECG waveform 12 of the display, and thus it is desirable to unwrap all of the endocardial surfaces from all of the 3D images of the heart cycle and arrange them in a "stack" so that the clinician can view them sequentially in any order. If the clinician spots a motional abnormality on one of the unwrapped images, such as in the area denoted by box 202, she can focus in on this cardiac wall location where the abnormality is seen. She can then scan through the stack of images in the box 202 in either temporal order to examine the abnormality in greater detail over the full heart cycle. Alternately, the clinician can draw a line through the abnormality in box 202, then display the tissue Doppler values along that line from all the images in the sequence in an ABD-TDI display 102 as described above.

Figure 15C:
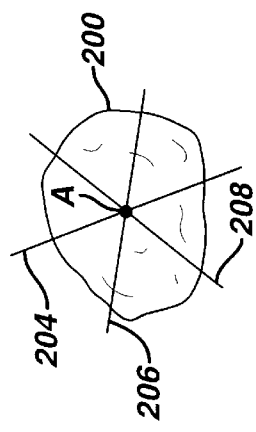

If real time 3D imaging capability is not available, a 3D diagnosis can still be performed by acquiring multiple image planes of a chamber of the heart at different orientations, which are then processed by automatic border detection. An ultrasound system which acquires ultrasound information from only selected planes of an organ of the body is described in U.S. patent application Ser. No. 09/641,306, entitled "METHOD OF CREATING MULTIPLANAR ULTRASONIC IMAGES OF A THREE DIMENSIONAL OBJECT." FIG. 15*c* is an illustration of the endocardial border 200 viewed from the apex A in the center of the drawing, which is how the heart may be viewed by a transducer probe placed for an apical view as described above. With the probe so located, ultrasound information is acquired from three planes which pass through the heart chamber, labeled 204, 206 and 208 in the drawing. In this drawing the planes are viewed edge-on, and in this example the three planes intersect in the vicinity of the apex of the LV. The ultrasound information from the three planes may be acquired at a particular phase of the heart cycle chosen by and ECG heart gate, or over the full cardiac cycle which may also be assisted by ECG gated acquisition over a number of cardiac cycles. The LV endocardial borders in the images of the three planes are automatically drawn as described above and analyzed.

Figure 15D:
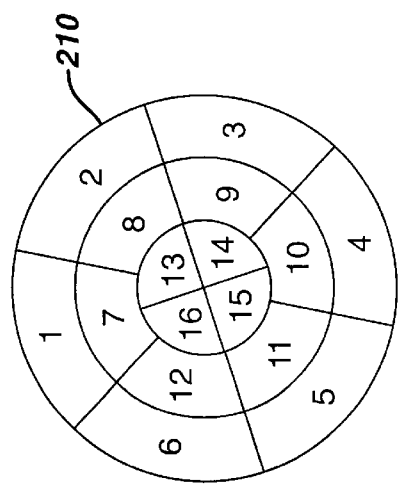
FIG. 15d illustrates a scorecard for scoring a three dimensional image of the heart.

A quick method for identifying a region of the heart where more detailed study is required is to score cardiac performance on a symbolic representation of the heart. One such symbolic representation is the bullet scorecard 210 shown in FIG. 15*d*. The scorecard 210 represents the heart muscle of a chamber of the heart as if the myocardium were spread out in a single plane with the apex at the center of the scorecard and the juncture of the myocardium and the mitral valve plane located around the perimeter of the scorecard. Each sector of the scorecard 210 extending from the center to the perimeter represents a different section of the heart muscle extending from the apex to the mitral valve plane. The areas in the scorecard are numbered to refer to specific areas of the heart wall. For instance the image plane 204 of FIG. 15*c* would intersect areas 1, 7, the center of the scorecard, and areas 10 and 4. The image plane 206 of FIG. 15*c* would intersect areas 6, 12, 16, 14, 9 and 3 of the scorecard, and the image plane 208 of FIG. 15*c* would intersect areas 5, 11, 15, 13, 8 and 2 of the scorecard. The Doppler-detected motion on an automatically drawn border in one or more image frames in the image planes is used to enter data in the scorecard 210. The scorecard is filled in automatically using the motion information from the automatically drawn borders to indicate areas of the heart where detailed diagnosis is warranted. For instance, if cardiac behavior in the plane 204 of the LV is normal, areas 1, 7, 10, and 4 can be displayed in green on the ultrasound system display. If an unusual characteristic such as abnormal motion is sensed in the vicinity of the juncture of the myocardium and the mitral valve plane, area 1 may be displayed in yellow (for mild irregularity) or red (for a serious irregularity), to caution the clinician to look more closely at this area. Numerical scores may be used in addition to or alternatively to color-coding. A preferred four-tiered scoring system for cardiac performance is to score regions of the heart muscle as being either normal, hypokinetic, dyskinetic, or akinetic. Thus the displayed bullet scorecard with its color-coded or numerically scored areas will point the clinician to regions of the heart where more detailed diagnosis should be performed.

It is preferable, of course, to use a complete 3D data set to fill in the scorecard 210. For instance, the defined heart wall 200 of FIG. 15a can be "flattened," and spread in a circle about the apex so that each area of the myocardium in the data set corresponds to an area of the scorecard. The motional data over a section of the flattened heart wall 200 can be averaged to fill in a corresponding section of the bullet scorecard 210. For example, the motional data over section 212 of the endocardial data 200 can be averaged to automatically compute a score (either quantitative or qualitative) for corresponding area 5 of the scorecard 210. The scores for section 212 from a plurality of endocardial data sets taken over the full heart cycle can also be averaged or outlying values detected to produce a scorecard of averages of cardiac performance or greatest degrees of abnormal performance.

Figure 16:
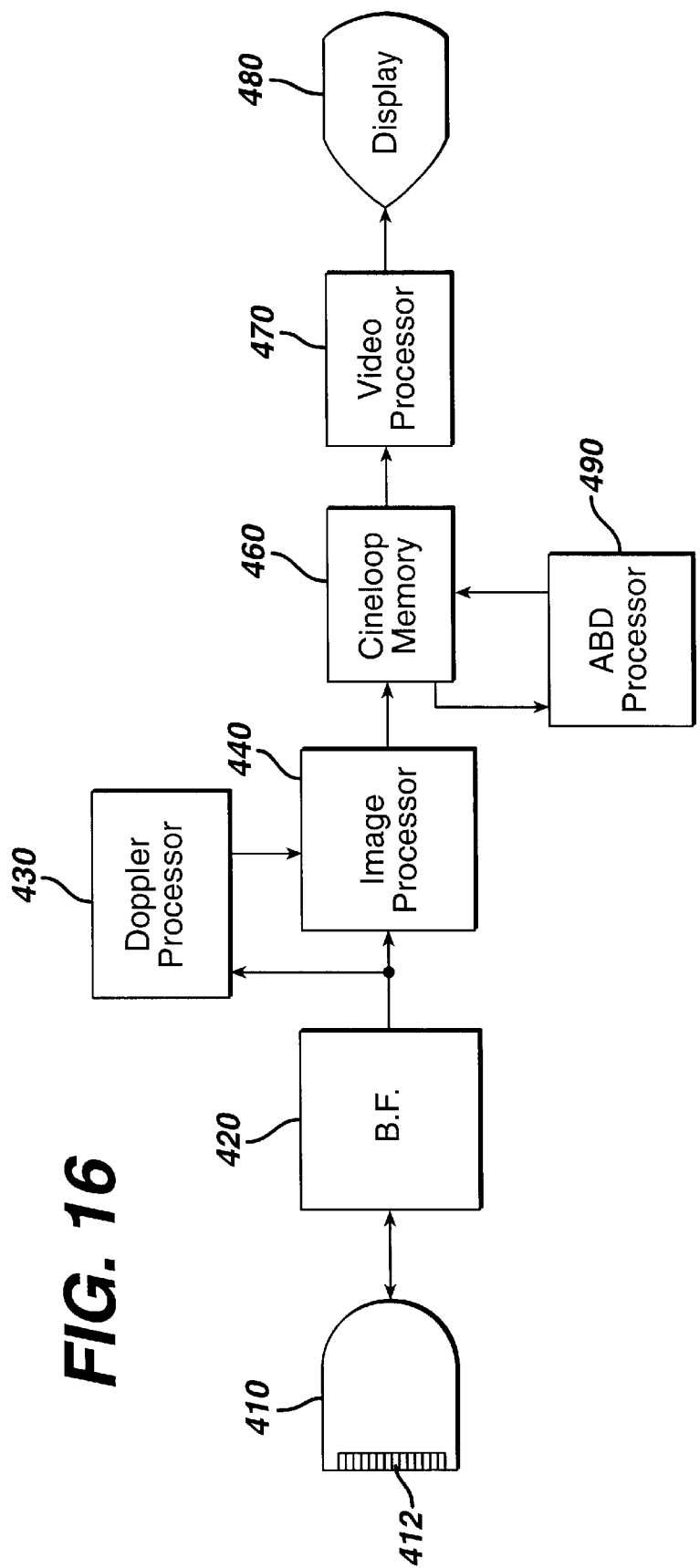
FIG. 16 illustrates in block diagram form an ultrasonic diagnostic imaging system constructed in accordance with the principles of the present invention.

FIG. 16 illustrates an ultrasound system constructed in accordance with the present invention. A probe or scanhead 410 which includes a 1D or 2D array transducer 412 transmits ultrasonic waves and received ultrasonic echo signals. This transmission and reception is performed under control of a beamformer 420 which processes in received echo signals to form coherent beams of echo signals from the anatomy being scanned. The echo information is Doppler processed by a Doppler processor 430 when ABD-TDI information or strain rate information is to be presented, and the processed Doppler information is coupled to an image processor 440 which forms 2D or 3D grayscale or Doppler images. The images pass through a Cineloop memory 460 from which they may be coupled directly to a video processor 470 for display on an image display 480. The images may also be applied to an ABD processor which operates on the 2D or 3D images as described above to define the anatomical borders and boundaries in the images. The defined borders are overlaid on the images which are coupled to the video processor 470 for display. The system may operate to define and display borders on loops of images saved in the Cineloop memory 460, or to display borders drawn on real time images produced during live scanning of a patient.

What is claimed is:

1. A method of analyzing ultrasonic images of the heart by border tracing comprising:

acquiring a sequence of images of a cardiac cycle which include at least an end diastole image and an end systole image;

displaying both the end diastole image and the end systole image on an image display; and automatically defining a border of the heart for at least one of the end diastole and the end systole images.

2. The method of claim 1, wherein the sequence of images includes a plurality of intervening images acquired between the times of acquisition of the end diastole and end systole images; and wherein automatically defining comprises:

automatically defining a border for the end systole image;

automatically defining borders for the intervening images by use of the results of defining the border for the end systole image; and then automatically defining a border for the end diastole image.

3. The method of claim 1, wherein the automatically defined border of the heart is the endocardial border.

4. The method of claim 3, further comprising computing the ejection fraction of the heart from the automatically defined endocardial borders of the end diastole and the end systole images.

5. The method of claim 4, further comprising displaying the computed ejection fraction together with the end diastole and end systole images.

6. The method of claim 5, further comprising manually adjusting the automatically defined border on one of the images; and automatically updating the displayed computed ejection fraction in response to a manual adjustment of an automatically defined border.

7. The method of claim 1, further comprising acquiring an ECG waveform of the cardiac cycle during which a sequence of images is acquired; and utilizing the acquired ECG waveform to automatically select the end diastole and end systole images for display.

8. The method of claim 7, further comprising:

reviewing one or more images which are temporally adjacent to the automatically selected end diastole or end systole images; and replacing one of the automatically selected images with one of the reviewed images.

9. A method of analyzing ultrasonic images of the heart by border tracing comprising:

acquiring a sequence of images of a cardiac cycle which include at least one of an end diastole image and an end systole image;

displaying at least one of the end diastole image and the end systole image on an image display;

displaying a tracing of a border of the heart on the displayed image; and replaying at least a portion of the sequence of images in succession while the tracing remains displayed.

10. The method of claim 9, wherein the sequence of images which is replayed is replayed in real time behind the displayed tracing.

11. The method of claim 9, wherein the sequence of images which is replayed is replayed at a frame rate of display which is slower than real time behind the displayed tracing.

12. The method of claim 9, wherein the myocardium of the replayed images appears to move inward from and then outward to the border tracing of an end diastole image.

13. The method of claim 9, wherein the myocardium of the replayed images appears to move outward from and then inward to the border tracing of an end systole image.

14. A method of automatically tracing borders of tissue in ultrasonic images comprising:

acquiring a sequence of cardiac loops of ultrasound images with an ultrasound probe;

manipulating the probe until the heart is displayed in the images in an orientation suitable for automatic border tracing;

processing at least one image of each cardiac loop while the probe is being manipulated to attempt to automatically trace a desired cardiac border; and displaying the at least one image together with a successfully traced cardiac border.

15. The method of claim 14, wherein only one image of each cardiac loop is processed; and
   wherein a succession of images from respective cardiac loops are successively displayed with the results of attempted automatic border tracing.

16. The method of claim 15, wherein the succession of images are displayed as thumbnail images.

17. The method of claim 14, wherein the images of the acquired cardiac loops are displayed in real time;
   wherein all of the images of each cardiac loop are processed; and
   wherein tracings are displayed on successfully traced borders in real time.

18. A method of automatically tracing borders of tissue in ultrasonic images comprising:
   acquiring a sequence of cardiac loops of ultrasound images with an ultrasound probe;
   displaying the images of the cardiac loops in real time;
   processing at least one image of each cardiac loop to attempt to automatically trace a cardiac border of the image; and
   simultaneously displaying an indicator showing the success of the processing.

19. The method of claim 18, wherein the indicator comprises an ejection fraction measurement.

20. The method of claim 18, wherein the indicator is a subjective indicator.

21. The method of claim 20, wherein the indicator indicates the success by a color indication.

22. The method of claim 18, wherein the indicator is an objective indicator.

23. The method of claim 22, wherein the indicator indicates the percentage of success.

24. The method of claim 18, wherein the indicator comprises a gauge display.

25. A method of automatically tracing borders of tissue in ultrasonic images comprising:
   acquiring a sequence of real time ultrasound images with an ultrasound probe;
   displaying the images in real time;
   processing at least one image to attempt to automatically trace a feature in the image;
   displaying a measure of the success of the processing;
   manipulating the probe until the displayed measure is above a desired level; and
   storing a selected sequence of images in an image memory when the success of the processing is above the desired level.

26. The method of claim 25, wherein the measure is a qualitative measure.

27. The method of claim 25, wherein the measure is a quantitative measure.

28. The method of claim 25, wherein the measure is displayed in a gauge display format.

29. The method of claim 25, wherein the measure is displayed as a tissue border tracing.

30. The method of claim 25, wherein the ultrasound images comprise ultrasound images of the heart.

31. The method of claim 30, wherein the feature is a border of the myocardium.

* * * * *